United States Patent [19]  [11] 4,378,352
Kimchi et al. [45] Mar. 29, 1983

[54] (2'-5')OLIGO-ISOADENYLATE PHARMACEUTICAL COMPOSITIONS AND METHOD OF USE

[75] Inventors: Adi Kimchi, Raanana; Michel Revel, Rehovot; Sara Rappoport; Yehuda Lapidot, both of Jerusalem, all of Israel

[73] Assignee: Yeda Research & Development Co. Ltd., Rehovot, Israel

[21] Appl. No.: 195,057

[22] Filed: Oct. 8, 1980

[30] Foreign Application Priority Data

Oct. 9, 1979 [IL] Israel .................................. 58421

[51] Int. Cl.³ ..................... A61K 19/20; C12P 19/34
[52] U.S. Cl. .................................. 424/180; 435/91; 536/27
[58] Field of Search .......................... 536/27; 424/180

[56] References Cited

U.S. PATENT DOCUMENTS 3,459,637  8/1969  Laufer et al. ................... 536/27
3,850,749  11/1974  Kaufmann et al. ............... 536/27
4,210,746  7/1980  Kerr et al. ....................... 536/27

Primary Examiner—Johnnie R. Brown
Attorney, Agent, or Firm—Browdy and Neimark

[57] ABSTRACT

The invention relates to a novel process for the production of $(2'-5')A(pA)_n pA$ chains wherein n is an integer of from 1 to 6, which comprises polymerizing adenosine (2'-3') monophosphate to obtain a mixture of 2'-5'- and 3'-5'-polyadenylic acid, treating the mixture with ribonuclease $P_1$ to cleave selectively the 3'-5'-bonds so as to retain the 2'-5'-polymeric moieties with a terminal 5'-phosphate moiety and removing the terminal phosphate groups by means of alkaline phosphatase. The mixture may be purified by separation on an anionic ion exchanger and collecting the individual fractions. The invention further relates to pharmaceutical compositions for inhibiting the immune response of mammals which comprise as active ingredient a (2'-5')oligo-isoadenylate defined above. The preferred compositions are those with a preponderance of the trimer.

7 Claims, No Drawings

(2'-5')OLIGO-ISOADENYLATE PHARMACEUTICAL COMPOSITIONS AND METHOD OF USE

FIELD OF THE INVENTION

The present invention relates to the production of (2'-5') A(pA)$_n$pA chains, wherein n is an integer of from 1 to 6, and to pharmaceutical compositions containing such compounds as active ingredient.

A preferred process for the production of the above polymerizing adenosine (2'-3') monophosphate to obtain a mixture of 2'-5'-polyadenylic acid, treating the mixture with ribonuclease P$_1$ to cleave selectively the 3'-5'-bonds so as to retain the 2'-5'-polymeric moieties with a terminal 5'-phosphate moiety, removing terminal phosphate groups by means of alkaline phosphatase and if desired subjecting the resulting mixture to separation on an anionic ion-exchanger and collecting the individual fractions.

Amongst preferred fractions prepared and collected according to the process of the present invention there are: (2'-5')ApApA; (2'-5')ApApApA; (2'-5')ApApApApA and (2'-5')ApApApApApA; also compounds of the type (2'-5')ppp(Ap)$_n$A wherein n is an integer of 1 to 6 are of value as active compounds.

The novel pharmaceutical compositions according to the present invention are of value in inhibiting the immune response of mammals, and specifically of humans for use with patients about to undergo surgical transplantations, for immuno-suppressive action in immune diseases and the like. The preferred fractions of the above defined compounds are the trimers, with value also of the tetramers, and lesser value of other constituents.

State of the Prior Art

Immunosuppression is required to prevent excessive immune reaction in autoimmune diseases and in transplantation.

Formerly used drugs are antimetabolites such as derivatives of cyclophosphamide or 6-mercaptopurine. These agents have a general toxic effect on cells.

Interferon induces in cells an enzyme which converts ATP into (2'-5')pppApApA, or oligo-isoadenylate (Kerr and Brown, Proc. Natl. Acad. Sci. USA 75, 256, 1978; Zilberstein et al., Proc. Natl. Acad. Sci. USA 75, 4734, 1978). The oligonucleotide causes an inhibition of protein synthesis in cells permeabilized by hypotonic shock (Williams and Kerr, Nature 276, 88, 1978). No effects on *intact* non-permeabilized cells have been described.

SUMMARY OF THE INVENTION

The present invention relates to a process for the production of (2'-5')A(pA)$_n$pA chains, wherein n is an integer of 1 to 6, which comprises polymerizing adenosine (2'-3')-monophosphate to obtain a mixture of 2'-5'-polyadenylic acid, treating the mixture with ribonuclease P$_1$ to cleave selectively the 3'-5'-bonds so as to retain the 2'-5'-polymeric moieties with a terminal 5'-phosphate moiety, removing terminal phosphate groups by means of alkaline phosphatase and if desired subjecting the resulting mixture on an anionic ion exchanger and collecting the individual fractions.

The present invention further relates to various specific fractions obtained by the said process. Furthermore, the invention relates to pharmaceutical compositions of matter which contain as active ingredient synthetic oligonucleotides of the type defined above, either as mixtures of chains of varying length, or as individual fractions. The products of the invention can be designated by the formula (2'-5')A(pA)$_n$pA wherein n is an integer of 1 to 6. The preferred chains are the trimers, while the tetramers and pentamers are also of substantial value.

The novel synthetic oligonucleotides are of value as inhibitors of the mitogenesis of lymphocytes. Mitogenesis, or entry of resting non-dividing cells in the S-phase in which DNA synthesis takes place, is the first step of the immune response. Lymphocytes exposed to antigens, allogeneic cells, or lectins, undergo mitogenesis. In many pathological cases, this mitogenic response should be inhibited or reduced; for example, in autoimmune diseases or in transplantation medicine. The invention will be illustrated with reference to the inhibition of spleen lymphocyte mitogenic response to a lectin, Concanavalin A. The specific and potent effect of minute amounts of chemically synthesized (2'-5') oligoisoadenylate added to the cell cultures illustrates the potential of this new type of compound for use in the treatment of the above mentioned and other diseases. Other derivatives of (2'-5')ApApA, as those in which the chain is longer, or the molecules have been further modified by alkylation or other chemical modification, form a new family of compounds with important biological activities.

The (2'-5') oligo-isoadenylate pppApApA is a natural product made by an enzyme which is induced in cells of human or animal origin by interferon treatment. The oligonucleotide can be synthesized chemically and has the same biological activity, i.e., activation of ribonuclease F, as the natural compound (Schmidt, et al., FEBS Letters 95, 257, 1978). The discovery that (2'-5') oligo-isoadenylate, without the 5' triphosphate, inhibits the mitogenic response in intact lymphocytes makes it particularly useful in accordance with the present invention. Interferon is known to decrease cell proliferation and to act as a regulator of the immune response (Gresser and Tovey, Biochim. Biophys. Acta 516, 231, 1978). The use of (2'-5') oligo-isoadenylate, instead of interferon, is of advantage (1) because the chemical is synthesized easily and in large quantity, (2) because it probably mediates only one of the effects of interferon and would be expected to have less secondary effects than interferon itself.

The inhibition of lymphocyte mitogenesis by (2'-5') oligo-isoadenylate can be applied in several pathogenic conditions. Auto-immune diseases (such as, for example, myasthemia gravis, allergic encephalomyelititis, etc.) are due to an excessive response of lymphocytes to host antigens. These diseases can be treated by immunosuppressive drugs. Such drugs are usually toxic antimetabolite compounds which interfere rather generally with DNA synthesis. Immunosuppressive drugs, such as derivatives of mercaptopurines have many side effects on the patient's body, as a result of this toxicity. Oligo-isoadenylate being the natural mediator of interferon's effect, would be expected to be much less toxic, have a more specific effect (i.e., no inhibition of other cells) and be as effective as an immunosuppressive drug. Other indications for immunosuppression, as in transplantation medicine, may be also areas where oligo-isoadenylate would find its use. The optimum dosage of the oligoisoadenylate in the treatment of such conditions is 20 to 500 mg/human/day.

DETAILED DESCRIPTION OF THE INVENTION

The present invention will be illustrated with reference to the following Examples, which are to be construed in a non-limitative manner.

The Examples illustrate the preparation of the (2'-5') oligo-isoadenylate moieties and to the effect of oligonucleotides as active ingredients of pharmaceutical compositions, and especially for inhibiting the immune response of lymphocytes. Various other applications, as set out above, are within the ambit of the present invention.

A. CHEMICAL SYNTHESIS OF (2'-5') OLIGO-ISOADENYLATE

EXAMPLE 1: (2'-5')ApApA and longer oligomers

The tri-n-butylammonium salt of adenosine 2-3' cyclic phosphate was polymerized into poly A containing random distribution of 2'-5' and 3'-5' phosphodiester bonds according to Michelson (Biochemical Preparation, p. 131), 250 mg of this poly A in 25 ml of 0.1 M acetate buffer pH 5.8 was incubated with 5 mg ribonuclease $P_1$ for 1 hour at 60° C. The solution (7,500 $A_{260}$) was cooled, diluted to 125 ml with 0.02 M ammonium bicarbonate and applied to a DEAE-Sephadex A-25 column ($HCO_3^-$ form, 2.5×45 cm). Elution was done with a 6 l linear gradient of 0.02–0.4 M ammonium bicarbonate, followed by a 4 l linear gradient of 0.35–0.5 M ammonium bicarbonate. 20 ml fractions were collected at 1.3 ml/min. Peaks showing $A_{260}$ absorbance were collected, flash evaporated and lyophilized. The compounds were identified by treatment with bacterial alkaline phosphatase (BAP) followed by hydrolysis with 0.6 M KOH overnight at 37° C. and the ratio of adenosine to adenosine 2 (3') phosphate determined to measure chain lengths (Table 1). The $R_F$ on paper chromatography in n-propanol:ammonia:water (55:10:35) were characteristic of (2'-5') oligo A (Table 1). The oligonucleotides were resistant to RNase $T_2$, but sensitive to the 2'-phosphodiesterase described by Schmidt et al., (FEBS Letters 95, 257–264, 1978).

Peaks 5–8 of Table 1 were treated (at a concentration of 1 mM oligonucleotides) with 30 U/ml BAP in 30 mM tris-base (pH 8), 30 min at 37° C., to obtain (2'-5')APA (dimers), ApApA (trimers), ApApApA (tetramers) or longer chains.

EXAMPLE 2: (2'-5')pppApApA

This compound was obtained by chemical phosphorylation of (2'-5')pApApA. Tetra sodium pyrophosphate (2 mmoles) was passed on a Dowex 50W-X4 column (pyridinium form, 1.2×40 cm) and eluted with water. To 100 ml of eluate, 2 mmoles tri-n-butylamine were added and the solution was flash evaporated. The material was coevaporated 3 times with pyridine and twice with dimethyl-formamide (DMF). To 2,600 $A_{260}$ of (2'-5')pApApA, 0.1 ml tri-n-butylamine was added and the material dissolved in 7 ml absolute methanol. The solvent was evaporated and 3 coevaporations with DMF were done. The residue was dissolved in 7 ml DMF and 0.1 ml diphenyl phosphochloridate and tri-n-butylamine were added. The clear solution was kept at room temperature 3 hours, flash evaporated and treated with ether. The residue was dissolved in 7 ml DMF and 0.2 mmole of the tri-n-butylammonium salt of pyrophosphoric acid (prepared above) was added. After 1 hour at room temperature, the solution was evaporated and treated with ether. The dry powder was dissolved in $H_2O$ and chromatographed on a DEAE-Sephadex A-25 column ($HCO_3^-$ form; 1.2×45 cm). A 1,500 ml linear gradient of NaCl 0.04 M was used for elution followed by a second gradient of NaCl 0.4–0.6 M. Fractions of 10 ml were collected at 0.5 ml/min. The main $A_{260}$ peak eluting at 0.43 M NaCl was evaporated to dryness, dissolved in water and desalted on a Biogel P2 column (2.5×40 cm). 770 $A_{260}$ were recovered in the excluded peak and lyophilized. The (2'-5')pppApApA was characterized by chromatography on a DEAE-cellulose column (0.6×40 cm) in 50 mM Tris-HCl pH 7.6, 50 mM NaCl, 7 M urea with a 150 ml gradient of 0.05–0.2 M NaCl. The material eluted between charges −5 and −6, as the enzymatically synthesized (2'-5')pppApApA (Schmidt et al., FEBS Letters 95, 257–264, 1978), was desalted on DEAE-cellulose with ammonium bicarbonate (Tener, Methods in Enzymol. 12, 398–404, 1967) and lyophilized.

EXAMPLE 3

(3'-5')ApApA and longer oligomers were prepared from poly A synthesized from ADP with polynucleotide phosphorylase. This poly A contains only (3'-5') phosphodiester bonds. Oligonucleotides were prepared by a partial ribonuclease $P_1$ hydrolysis followed by bacterial alkaline phosphatase and fractionation on DEAE-Sephadex as in Example 1. (3'-5')pppApApA prepared from the pApApA obtained after a partial ribonuclease $P_1$ hydrolysis as above and in Example 2.

Inhibition of the immune response of lymphocytes by (2'-5') oligo-isoadenylate

A convenient method to measure the immune response of lymphocytes is to use Concanavalin A (Con A) stimulation of mitogenesis in fresh spleen lymphocytes. The mitogenic response is the first part of the immune response which occurs when the organism is exposed to an antigen. It is a common step for both the humoral and the cellular immune response. Agents which inhibit mitogenesis in antigen or lectin-stimulated lymphocytes have usually strong immunosuppressive effects. The following examples show that (2'-5') oligo-isoadenylate inhibits Con A-stimulated mitogenesis.

EXAMPLE 4

Mouse spleen lymphocytes ($8 \times 10^6$ cells/ml) were exposed to Concanavalin A (2.5 μg/ml) in culture medium RPMi 1640 or DMEM (Gibco, Grand Island), with 5% heat inactivated fetal calf serum. After 10 min at 37° C., chemically synthesized (2'-5')ApApA was added at concentrations of $2-10 \times 10^{-6}$ M and incubation continued for 3 days. The mitogenic response was measured by adding 6 μCi/ml of [$^3$H]-thymidine (5 Ci/mmol) for 3 hours and by measuring incorporation of radioactivity into DNA. Cells were harvested on glass fiber filters, washed twice with 5 ml cold phosphate buffered saline, twice with 5 ml of 5% trichloro active acid, once with 95% ethanol, dried and counted.

Table 2 shows that in the pressure of (2'-5')ApApA there was a very strong inhibition of the mitogenic response. The effect was observed with concentrations of $10^{-5}$ of the oligonucleotide and does not require pretreatment of the lymphocytes. In contrast, the (3'-5')

isomer had no inhibitory activity on the lectin-induced mitogenic response of lymphocytes.

EXAMPLE 5

The time of addition of the (2'-5') oligo A was studied. Addition of 5 μM (2'-5')ApApApA, 24 hours after the Con A-stimulus produced the same inhibition as when it is given at time zero. At 48 hours, however, the ability of the oligonucleotide to inhibit mitogenesis is much reduced. DNA synthesis starts to increase at 48 hours and peaks at 72 hours. This result indicates that the (2'-5') oligonucleotide inhibits the entry of cells into the S-phase of the cell cycle. In this synchronized system, the cells have all entered the S-phase at 48 hours. In the organism, where such synchronization does not occur, the (2'-5') oligo A should be an effective blocker of mitogenesis even if given after the immunostimulus has begun to act.

EXAMPLE 6

Oligonucleotides of various chain lengths were compared. The trimer, tetramer and pentamer of (2'-5') oligo-isoadenylate were added to cultures of spleen lymphocytes 10 minutes after adding 2.5 μg/ml Concanavalin A. At 72 hours of culture, the synthesis of DNA was measured. Table 3 shows that all (2'-5') isoadenylate oligomers were active. The trimer was, however, somewhat more active at low concentrations. This may be due to a better penetration into the cells.

TABLE 1

Separation of chemically synthesized (2'-5') oligo-isoadenylate by chromatography on DEAE-Sephadex

| Peak Number | eluted at $NH_3HCO_3$ | Percent of total $A_{260}$ applied to column | Compound | $R_f^{a'}$ | BAP + KOH Ap | A |
|---|---|---|---|---|---|---|
| | 0.05 M | 20 | Adenosine | | | |
| | 0.1 M | 14 | (2'-5')ApA | | | |
| | 0.2 M | 24 | (5')pA | 1 | 0 | 1 |
| | 0.21 M | 4 | unidentified | | | |
| | 0.28 M | 13 | (2'-5')pApA | 0.87 | 0.98 | 1 |
| | 0.34 M | 6 | (2'-5')pApApA | 0.74 | 1.71 | 1 |
| | 0.37 M | 5 | (2'-5')pApApApA | 0.65 | 3.03 | 1 |
| | 0.4 M | 5 | (2'-5')pApApApApA | | | | in n propanol:ammonia:water (55:10:35).

TABLE 2

Inhibition of DNA Synthesis by (2'-5') oligo-isoadenylate in Con A-stimulated Mouse Spleen Lymphocytes

| Culture | | DNA synthesis at 72 h [$^3$H]—thymidine incorporated counts/min |
|---|---|---|
| 1. Untreated | | 28,760 |
| 2. +Con A 2.5 μg/ml | | 139,775 (100) |
| 3. +Con A + (2'-5')ApApA, | 2 μM | 50,175 (19) |
| | 5 μM | 41,805 (12) |
| 4. +Con A + (3'-5')ApApA | 5 μM | 142,665 (102) |
| | 10 μM | 142,295 (102) |

Nucleotides added to lymphocyte cultures 10 min after Con A.

TABLE 3

Effect of Different Oligonucleotides on DNA Synthesis in Con A-stimulated Mouse Spleen Lymphocytes

| Oligo A added | Final concentration μM | Inhibition of incorporation of $^3$H—thymidine % |
|---|---|---|
| None | — | 0 |
| (2'-5') trimer A2'p5'A2'p5'A | 2 | 81 |
| | 5 | 88 |
| | 10 | 87 |
| (3'-5') trimer A3'p5'A3'p5'A | 5 | 0 |
| | 10 | 0 |
| (2'-5') tetramer A2'p5'A2'p5'A2'p5'A | 1 | 0 |
| | 5 | 50 |
| | 10 | 73 |
| (2'-5') pentamer A2'p5'A2'p5'A2'p5'A2'p5'A | 5 | 64 |
| | 10 | 94 |

Mouse spleen lymphocytes (8 × 10$^6$ cells/ml) were treated with 2.5 μg/ml Con A and 10 min later the different oligonucleotides (chemically synthesized as described) were added. DNA synthesis was measured at 72 h.
The total $^3$H—thymidine counts per min incorporated into TCA insoluble material of 1 ml suspension in the absence of any oligonucleotide was 125,000 cpm for the stimulated lymphocytes. Percent inhibition was calculated after the values of unstimulated cells (32,800 cpm) was subtracted.

We claim:

1. A pharmaceutical composition for inhibiting the immune response of mammals, which comprises as active ingredient an effective dosage of at least one (2'-5')-oligo-isoadenylate of the formula (2'-5')A(pA)$_n$pA wherein n is an integer of 1-6, and a pharmaceutically acceptable excipient.

2. A pharmaceutical composition according to claim 1, comprising as active ingredient about 20 to 500 mg/human/day.

3. A pharmaceutical composition according to claim 1, wherein said active ingredient is a combination of said (2'-5')-oligo-isoadenylates including trimer, tetramer and pentamer and wherein said trimer is present in the preponderant amount.

4. A method for inhibiting the immune response of mammals, comprising administering to a mammal in need of such inhibition an effective amount of at least one compound of the formula (2'-5')A(pA)$_n$pA wherein n is an integer of 1-6.

5. A method in accordance with claim 4 wherein said compound is administered to a human patient in an amount of 20 to 500 mg/day.

6. A method in accordance with claim 4 wherein the mammal being treated is one with an autoimmune disease.

7. A method in accordance with claim 4 wherein the mammal being treated is one about to undergo surgical transplantation.

* * * * *